United States Patent
Bruce et al.

(10) Patent No.: US 10,373,704 B2
(45) Date of Patent: Aug. 6, 2019

(54) REDUCTION OF SURFACE NUCLEOTIDE HYBRIDIZATION BY OPTIMIZING A BIOSENSOR SENSING SURFACE AREA

(71) Applicant: INTERNATIONAL BUSINESS MACHINES CORPORATION, Armonk, NY (US)

(72) Inventors: Robert L. Bruce, White Plains, NY (US); Payel Das, Yorktown Heights, NY (US); HsinYu Tsai, White Plains, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 168 days.

(21) Appl. No.: 15/172,801

(22) Filed: Jun. 3, 2016

(65) Prior Publication Data
US 2017/0349941 A1  Dec. 7, 2017

(51) Int. Cl.
| | |
|---|---|
| *G16B 25/00* | (2019.01) |
| *C12Q 1/6837* | (2018.01) |
| *G01B 21/28* | (2006.01) |
| *C12Q 1/6832* | (2018.01) |
| *C12Q 1/6834* | (2018.01) |

(52) U.S. Cl.
CPC .......... *G16B 25/00* (2019.02); *C12Q 1/6837* (2013.01)

(58) Field of Classification Search
CPC .................................................. C12Q 1/6832
See application file for complete search history.

(56) References Cited

U.S. PATENT DOCUMENTS

| | | |
|---|---|---|
| 5,821,060 A | 10/1998 | Arlinghaus et al. |
| 6,342,359 B1 | 1/2002 | Lee et al. |
| 7,101,671 B2 | 9/2006 | Gao |
| 2003/0013203 A1 | 1/2003 | Jedrzejewski et al. |
| 2004/0028875 A1 | 2/2004 | Van Rijn et al. |
| 2004/0101845 A1* | 5/2004 | Collins ............. C12Q 1/6876 435/6.11 |

(Continued)

OTHER PUBLICATIONS

IBM: List of IBM Patents or Patent Applications Treated as Related (Appendix P), Jun. 6, 2016, pp. 1-2.

(Continued)

*Primary Examiner* — Manuel L Barbee
*Assistant Examiner* — Raymond L Nimox
(74) *Attorney, Agent, or Firm* — Reza Sarbakhsh (57) ABSTRACT

A method, computer program product, and system for identifying a surface area size of a biosensing structure, for use in a biosensor device, based on a plurality of nucleotides structures under test. A first set of properties are determined comprising: reaction coordinate values, and potential of mean force (PMF) values, for the plurality of nucleotide structures based on a first set of testing conditions comprising a first surface area material, a first surface area pattern, and a first surface area size. A second set of properties is determined comprising reaction coordinate values, and PMF values, for the plurality of nucleotide structures based on a second set of testing conditions comprising a second surface area material, a second surface area pattern, a second surface area size, or a combination thereof and a target population of nucleotide structures among the plurality of nucleotide structures are identified.

18 Claims, 4 Drawing Sheets

(56) References Cited

U.S. PATENT DOCUMENTS

| | | | | |
|---|---|---|---|---|
| 2004/0101846 | A1* | 5/2004 | Collins | G06F 19/20 435/6.12 |
| 2005/0095596 | A1* | 5/2005 | Leproust | B01J 19/0046 435/6.12 |
| 2007/0099198 | A1* | 5/2007 | Hassibi | G06F 19/20 435/6.12 |
| 2008/0027654 | A1* | 1/2008 | Nelson | G06F 19/22 702/20 |
| 2010/0234235 | A1* | 9/2010 | Kaplan | C40B 60/12 506/7 |
| 2016/0281149 | A1* | 9/2016 | Hassibi | C12Q 1/6837 |

OTHER PUBLICATIONS

Bruce et al., Pending U.S. Appl. No. 15/172,737, filed Jun. 3, 2016, titled "Biosensor for Optical Detection of Nucleotide Sequence,", pp. 1-36.

Bruce et al., Pending U.S. Appl. No. 15/172,759, filed Jun. 3, 2016, titled "Biosensor for Electrical Detection of a Nucleotide Sequence,", pp. 1-46.

Anne et al., "Dynamics of Electron Transport by Elastic Bending of Short DNA Duplexes. Experimental Study and Quantitative Modeling of the Cyclic Voltammetric Behavior of 3'-Ferrocenyl DNA End-Grafted on Gold," J. Am. Chem. Soc. 2006, Copyright 2006 American Chemical Society, pp. 542-557.

Kaiser et al., "Conformations of End-Tethered DNA Molecules on Gold Surfaces: Influences of Applied Electric Potential, Electrolyte Screening, and Temperature," J. Am. Chem. Soc. 2010, Copyright 2010 American Chemical Society, pp. 7935-7945.

Li et al., "Separation of DNA with Different Configurations on Flat and Nanopatterned Surfaces," Analytical Chemistry, vol. 78, No. 14, Jul. 15, 2006, Copyright 2006 American Chemical Society, pp. 4743-4751.

Peterson et al., "The effect of surface probe density on DNA hybridization," Nucleic Acids Research, 2001, vol. 29, No. 24, Copyright 2001 Oxford University Press, pp. 5163-5168.

Petrovykh et al., "Quantitative Analysis and Characterization of DNA Immobilized on Gold," J. Am. Chem. Soc., 2003, Copyright 2003 American Chemical Society, pp. 5219-5226.

Relogio et al., "Optimization of oligonucleotide-based DNA microarrays," Nucleic Acids Research, 2002, vol. 30, No. 11, Copyright 2002 Oxford University Press, pp. 1-10.

Sakata et al., "Potential Behavior of Bio-chemically Modified Gold Electrode for Extended Gate Field Effect Transistor," National Institute for Materials Science, Tsukuba, Ibaraki, Japan, Japanese Journal of Applied Physics (Impact Factor: 1.13), DOI: 10.1143/JJAP.44.2860, pp. 1-4.

Zhou et al., "Use of Atomic Force Microscopy for Making Addresses in DNA Coatings," Langmuir 2002 Copyright 2002 American Chemical Society, Published on Web Sep. 26, 2002, pp. 8278-8281.

Ruiz et al., "Density Multiplication and Improved Lithography by Directed Block Copolymer Assembly," Science, vol. 321, Aug. 15, 2008, pp. 936-939.

Cheng et al., "Pattern Registration Between Spherical Block-Copolymer Domains and Topographical Templates," Adv. Mater., 2006, vol. 18, Copyright 2006 Wiley-VCH GmbH & Co. KGaA, Weinheim, pp. 597-601.

Cheng et al., "Templated Self-Assembly of Block Copolymers: Effect of Substrate Topography," Adv. Mater., 2003, vol. 15, No. 19, Oct. 2, 2003, Copyright 2003 Wiley-VCH GmbH & Co. KGaA, Weinheim, pp. 1599-1602.

Das et al., "Mechanistic Influence of Nanometer Length-Scale Surface Chemistry on DNA Hybridization," ACS Nano, vol. 9, No. 7, Jun. 8, 2015, pp. 7466-7478, Grace Period Disclosure.

Chen et al., "Ionic strength-dependent persistence lengths of single-stranded RNA and DNA," PNAS, vol. 109, No. 3, Jan. 17, 2012, pp. 799-804.

Rechendorff et al., "Persistence length and scaling properties of single-stranded DNA adsorbed of modified graphite," The Journal of Chemical Physics, 131, 095103, 2009, Copyright 2009 American Institute of Physics, pp. 1-6.

Koltai et al., "Specificity of DNA microarray hybridization: characterization, effectors and approaches for data correction," Nucleic Acids Res., Apr. 2008; 36(7), Copyright 2008 The Author(s), pp. 2395-2405.

Fiche et al., "Temperature Effects on DNA Chip Experiments from Surface Plasmon Resonance Imaging: Isotherms and Melting Curves," Biophys J., Feb. 1, 2007; 92(3), Copyright 2007, Biophysical Society, pp. 935-946.

Chen et al., "Kinetics and thermodynamics of DNA hybridization on gold nanoparticles," Nucleic Acids Res., Jun. 2009; 37(11), Copyright 2009 The Author9(s), pp. 3756-3765.

Draghici et al., "Reliability and reproducibility issues in DNA microarray measurements," Trends Genet, Feb. 2006; 22(2), pp. 101-109.

Levicky et al., "Physicochemical perspectives on DNA microarray and biosensor technologies," Trends in Biotechnology, vol. 23, No. 3, Mar. 2005, Copyright 2005 Elsevier Ltd., pp. 143-149.

Chan et al., "The Biophysics of DNA Hybridization with Immobilized Oligonucleotide Probes," Biophysical Journal, vol. 69, Dec. 1995, Copyright 1995 by the Biophysical Society, pp. 2243-2255.

Dorvel et al., "Silicon Nanowires with High-k Hafnium Oxide Dielectrics for Sensitive Detection of Small Nucleic Acid Oligomers," HHS Public Access, Author manuscript, Published online Jun. 22, 2012, doi: 10.1021/nn301495k, http://www.ncbi.nlm.nih.gov/pmc/articles/PMC3412126/, Printed on Apr. 11, 2016, pp. 1-18.

Vora et al., "Directed Self-assembly of Topcoat-free, Integration-friendly High-X Block Copolymers," Journal of Photopolymer Science and Technology, vol. 27, No. 3 (2014), Copyright 2014PST, pp. 419-424.

Josephs et al., "Nanoscale Spatial Distribution of Thiolated DNA on Model Nucleic Acid Sensor Surfaces," ACS Nano, vol. 7., No. 4, Jospehs and Ye, Copyright 2013 American Chemical Society pp. 3653-3660.

Josephs et al., "Electric-Field Dependent Conformations of Single DNA Molecules on a Model Biosensor Surface," Nano Lett., 2012, Published: Sep. 10, 2012, Copyright 2012 American Chemical Society, pp. 5255-5261.

Mir et al., Abstract for "Sequence variation in genes and genomic DNA: methods for large-scale analysis", Annual Review of Genomics and Human Genetics (Annu Rev Genom Hum G), vol. 1, No. 1, pp. 329-360, Feb. 2000.

Homola, "Surface Plasmon Resonance Sensors for Detection of Chemical and Biological Species", Chem. Rev. 2008, vol. 108, pp. 462-493.

Liepold et al., "Electrically detected displacement assay (EDDA): a practical approach to nucleic acid testing in clinical or medical diagnosis", Anal Bioanal Chem (2008), vol. 391: pp. 1759-1772.

Hall, Book: "Biosensors", Prentice Hall advanced reference series: Engineering Against the Clock Biotechnology series, Prentice Hall 1991, 351 pages.

Schena, Overview of "Microarray Analysis", New York: Wiley-Liss, John Wiley & Sons, Inc., 2003, 654 pages, Clinical Chemistry, vol. 49, No. 6, 2003, pp. 1031-1033.

Edited by: Kazuaki Suzuki, Bruce W. Smith, "Microlithography", Science and Technology, Second Edition, CRC Press, 2007, Sidewall Image Transfer, pp. 93-94.

* cited by examiner

REDUCTION OF SURFACE NUCLEOTIDE HYBRIDIZATION BY OPTIMIZING A BIOSENSOR SENSING SURFACE AREA

Aspects of the present invention have been disclosed in a publication made available to the public on Jun. 8, 2015. Payel Das & Sufi Zafar, *Mechanistic Influence of Nanometer Length-Scale Surface Chemistry on DNA Hybridization*, 7466-478 (Jun. 8, 2015). The following disclosure is submitted under 35 U.S.C. § 102(b)(1)(A).

BACKGROUND

The present invention relates generally to the field of biochemistry, and more particularly to determining the optimal biosensing surface area to reduce false detection of nucleotides.

Surface hybridization, in which an immobilized probe single-stranded DNA (ss-DNA) of known sequence recognizes the complementary target ss-DNA (c-DNA) molecule, is central to DNA biosensing technologies and novel nanodevices. These techniques are being extensively applied in a number of important fields such as genotyping, gene expression profiling, and biological detection. Hybridization at the solid/liquid interface can be significantly promoted by the nonspecific adsorption of the target ss-DNA and the consequent two-dimensional search. Several other factors such as probe density, probe and linker length, surface topology, and surface chemistry further affect surface hybridization, thus making hybridization on surface more complicated than that in solution. However, if would be advantageous to design an optimal surface hybridization protocol.

Gold has been extensively used to study the interactions governing surface hybridization due to its many useful properties as a model substrate. However, hybridization on gold is affected by nonspecific adsorption of the exposed bases of small strand DNA or ss-DNA. Nonspecific DNA gold interaction is found to be base-dependent, following the order A>G>C>T. Typical probe sequences (nucleotides) at low surface densities exhibit hybridization efficiency of greater than 60% that is lower than what is observed in solution. A planar gold surface has been reported to significantly slow down and lower free energy of hybridization. Studies also suggested incomplete hybridization on gold. Due to typical probe sequences nonspecific interactions with gold, the use of gold, as presented in more detail below, in order to increase the sensitivity and accuracy of probe-gold interactions is not an obvious solution.

SUMMARY

Embodiments of the present invention disclose a method, computer program product, and system for identifying a surface area size of a biosensing structure, for use in a biosensor device, based on a plurality of nucleotides structures under test. A first set of properties are determined comprising: reaction coordinate values, and potential of mean force (PMF) values, for the plurality of nucleotide structures based on a first set of testing conditions comprising a first surface area material, a first surface area pattern, and a first surface area size. A second set of properties is determined comprising reaction coordinate values, and PMF values, for the plurality of nucleotide structures based on a second set of testing conditions comprising a second surface area material, a second surface area pattern, a second surface area size, or a combination thereof. A target population of nucleotide structures among the plurality of nucleotide structures are identified, the target population comprising nucleotide structures whose PMF values in the second set of properties are less than corresponding PMF values in the first set of properties.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Various embodiments of the present invention include a computer-implemented method, computer system, and computer program product for identifying a surface area size of a biosensing structure, for use in a biosensor device, based on a plurality of nucleotides structures under test. A computer simulation is performed of a system that contains (1) a probe nucleotide sequence attached to (2) a sensor surface, and (3) a target complementary nucleotide sequence added to the solution. The structures generated by computer simulation is then clustered based on a number of set of properties (reaction coordinates) of the nucleotide structures. The relative population of each of those clusters is determined is determined by computing Potential of Mean Force (PMF). The first set of r The first set of reaction coordinates is the center-to-center distance between two nucleotide, number of complementary base-pairs formed, angle between two strands, or a related variable that estimate extent of hybridization. The second set of reaction coordinates is variables that measure extent of surface adsorption and the nucleotide structural characteristics on sensor surface. PMF values are calculated by using the weighted histogram analysis method (WHAM). The first set of testing conditions include a first surface area material, a first surface area pattern, and a first surface area size of a biosensing structure.

A second set of structural properties are determined, based on PMF analysis as a function of same reaction coordinates, for the plurality of nucleotide structures, based on a second set of testing conditions that show enhanced surface adsorption of nucleotides compared to the first testing conditions. The second set of testing conditions include a second surface area material, a second surface area pattern, a second surface area size, or a combination thereof, for a biosensing device. Based on the PMF analysis, a target population of nucleotide structures is identified among the plurality of nucleotide structures, where the target population includes those nucleotide structures whose population (PMF value) in the second set of testing condition is higher (less) than corresponding PMF values in the first set of testing condition and mostly represent the fully hybridized structures.

A third set of properties are determined including a third set of reaction coordinate values, and PMF values, for at least the target population of nucleotide structures, based on a third set of testing conditions including a third surface area material, a third surface area pattern, a third surface area size, or a combination thereof, for a biosensing device. A subset of the second and third sets of properties that have the greatest difference compared to the first set of properties are also identified.

In an embodiment, the first area material may include gold or silicon oxide, the first area pattern may be a sheet of various materials, for example, gold, or a set of dots made of various materials, for example gold. The size of the first surface area may be, in an embodiment, the measured area of the sheet and the surface area size for the plurality of dots may be the area of the top surface of the dot.

In various embodiments, the third surface area material may be the same as the second surface area material, and the third surface area pattern may be different from the second surface area pattern.

In various embodiments, the third surface area material is different from the second surface area material and the third surface area pattern is the same as the second surface area pattern. The third surface area material may be the same as the second surface area material, the third surface area pattern may be the same as the second surface area pattern, and the third surface area size may be different from the second surface area size.

In various embodiments, based on the PMF analysis, comparison between two different set of testing conditions, one or more population of nucleotide structures is identified among the plurality of nucleotide structures, which is different from the target population. Based on the free energy of hybridization, the positive or negative contribution of this non-target population toward full hybridization may be determined. The second and third sets of properties that have the greatest difference compared to the first set of properties are identified. The difference may be identified by determining the second and third sets of properties that have the lower PMF values below the PMF values of the first set of properties, identifying the second and third sets of properties with the largest negative slope, identifying the second and third sets of properties with the greatest delta value compared to the first set of properties, or identifying the second and third sets of properties with the lowest absolute PMF value.

In various embodiments, the lowest absolute value may not yield the desired result, therefore, a lowest absolute PMF value within a range bound be an upper or first threshold, and lower or second threshold, bound may be identified. The first threshold may be based a DNA probe length value and a max probe energy value. The second threshold may be the determined reaction coordinate value and a repulsive surface PMF value. The repulsive surface PMF value may be the calculated PMF of a silicon oxide surface.

The physical dimension of these low free energy, non-target population will determine the size of the optimal biosensor surface area. For a 23 base-pair long nucleotide, 6 nm is identified as the optimal sensor surface area. This size varies with the chemistry and length of the probe sequence. The lower bound of this size is related to twice the size (radius of gyration) of the ss-DNA on the surface, so that the hybridization is surface-mediated. The upper bound is determined by the end-to-end distance of the non-target population, so that the non-target population does not gain stability over the target population due to surface interaction. The upper and lower bounds may be identified from computer simulations.

A graphical representation based on the identified target population of nucleotide structures among the plurality of nucleotide structures is generated where the x-axis is the determined reaction coordinate value and the y-axis is the calculated PMF values. The graphical representation is presented to a user and a selection of a surface area value based on the generated graphical representation is received from the user.

Figure 1:
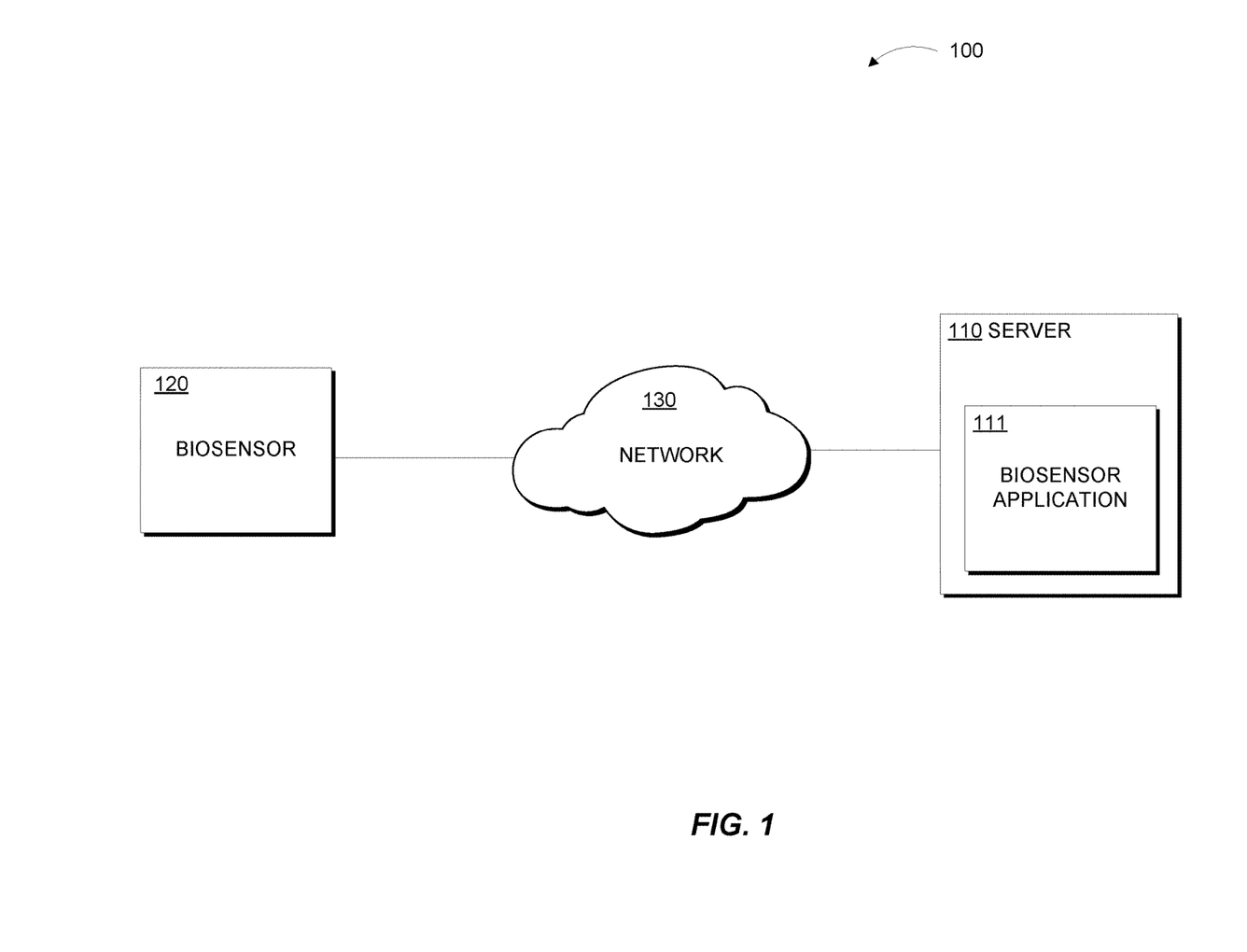
FIG. 1 is a functional block diagram illustrating a distributed data processing environment, in accordance with an embodiment of the present invention.

The present invention will now be described in detail with reference to the Figures. FIG. 1 is a functional block diagram illustrating a distributed data processing environment, generally designated 100, in accordance with one embodiment of the present invention.

Distributed data processing environment 100 includes server 110 and biosensor 120 all interconnected over network 130. Server 110 may act generally to host applications, for example, biosensor application 111 and may receive and communicate from biosensor 120 via network 130. Server 110 may be a laptop computer, tablet computer, netbook computer, personal computer (PC), a desktop computer, a smart phone, or any programmable electronic device capable of communicating with biosensor 120 via network. Server 110 includes biosensor application 111.

Biosensor application 111 may act generally to determine the optimal sensing surface area for a given probe, in accordance with an embodiment of the present invention. Biosensor application 111 may receive data on nucleotide sequences and environmental conditions, for example, attractive surface potential, repulsive surface potential, the bond strength, angle, and dihedral potentials of B-DNA crystal structures. In various embodiments, properties, persistence lengths, melting temperatures, and hybridization rate constants of nucleotide sequences are predetermined and pre-validated. Environmental conditions characterize the landscape of ss-DNA and ds-DNA hybridization.

In an exemplary embodiment, environmental condition data may be received by biosensor application 111 via server 110 including exemplary DNA potential values, for example 12-6 Lennard-Jones potential, attractive surface selection of gold with the potential (U) being $U_{gold}=4\varepsilon[(\sigma_{sur}/r_{sur})_{12}-(\sigma_{sur}/r_{sur})_6]$, with a cutoff distance of $r_c=12$ Å. The values of $\sigma_{sur}$ may be site-specific and may be determined by the combination rule $\sigma_{sur}=\frac{1}{2}(\sigma_{gold}+\sigma i)$, where $\sigma_{gold}=2.6$ Å and $\sigma_i$ is the VDW diameter of a particular site (i). The interaction strengths received may be site-dependent and set to $\varepsilon_{Phosphate\text{-}surface}=0.24$ kcal/mol, $\varepsilon_{Sugar\text{-}surface}=0.1$ kcal/mol, $\varepsilon_{A\text{-}surface}=4.0$ kcal/mol, $\varepsilon_{G\text{-}surface}=\varepsilon_{C\text{-}surface}=2.0$ kcal/mol, and $\varepsilon_{T\text{-}surface}=1.0$ kcal/mol. An exemplary repulsive surface selection of silicon oxide may be received with a potential with the form of $U_{repulsive}=4\varepsilon[(\sigma_{sur}/r_{sur})_{12}-(\sigma_{sur}/r_{sur})_6]+\varepsilon$, where $\varepsilon$ is set to 0.05 kcal/mol, where $r_{sur}$ is the distance between a particular base and the surface. The values of $\sigma_{sur}$ may be the same as the attractive surface values.

Biosensor application 111 may determine reaction coordinates for nucleotide sequences, where reaction coordinates are the center-to-center distance between two nucleotide strands. In various embodiments, the reaction coordinates may be predetermined, with values ranging, for example, between 10 Å and 138 Å. Biosensor application 111 may calculate the Potential of Mean Force (PMF) for nucleotide sequences. In various embodiments, the PMF may be based on reaction coordinates calculated by biosensor application 111 using the weighted histogram analysis method (WHAM), known in the art. The PMF represents the reversible work done to bring the perfect complementary nucleotide strands to the probe strand (free or surface-tethered) and hybridize. When the PMF is equal to zero, the two strands may have no interaction. As two strands approach each other, the free energy in bulk increases due to the like charge repulsion between the strand backbones and the entropic penalty related to the relative alignment of the strands needed for hybridization. In the ideal case, where no surface-dna interaction competes with dna-dna interaction, the free energy minimum may correspond to the hybridized state. When surface adsorption leads to partially hybridized, stable nucleotide structure formation, a number of free energy minima may exist, leading to false positives and/or false negatives.

Biosensor application 111 may determine the calculated PMF of hybridization values of nucleotide sequences on a number of surfaces that vary in dna adsorption, as described above. Biosensor application 111 may determine a range of reaction coordinates where the PMF of nucleotide sequences are between a first and second threshold. In various embodiments the thresholds may be predetermined, based on a received user selected range, based a generated graphical representation of the PMF and reaction coordinates of nucleotide sequences and repulsive surfaces, or reaction coordinate values. For example, the threshold range may be the range of reaction coordinate values where the calculated PMF of the nucleotide sequences are less than the repulsive potential described above. If the PMF of nucleotide sequences is less than the repulsive potential at reaction coordinates of 20 Å to 80 Å, the threshold may be from 20 Å to 80 Å.

Biosensor application 111 may generate a plurality of surface areas based on the PMF values between a first and second threshold described above. For example, if the determined threshold range is 20 Å to 80 Å, surface area values may be 2 nm to 8 nm where 1 Å=10 nm. Biosensor application 111 may determine the optimal surface area value based on the PMF values and surface area value range. For example, if the maximum differential between the PMF of the nucleotide sequences and repulsive potential occurs at 60 Å the optimal surface area value may be 6 nm.

Biosensor application 111 may receive probe self-assemble and hybridization measurements from a sensor, for example, biosensor 120. Biosensor 120 may act generally to communicate data to biosensor application 111 to confirm surface area selection. Biosensor 120 is described in more detail in reference to FIG. 4.

Network 130 can be, for example, a local area network (LAN), a wide area network (WAN) such as the Internet, or a combination of the two, and can include wired, wireless, or fiber optic connections. In general, network 130 can be any combination of connections and protocols that will support communications between server 110 and biosensor 120.

Figure 2:
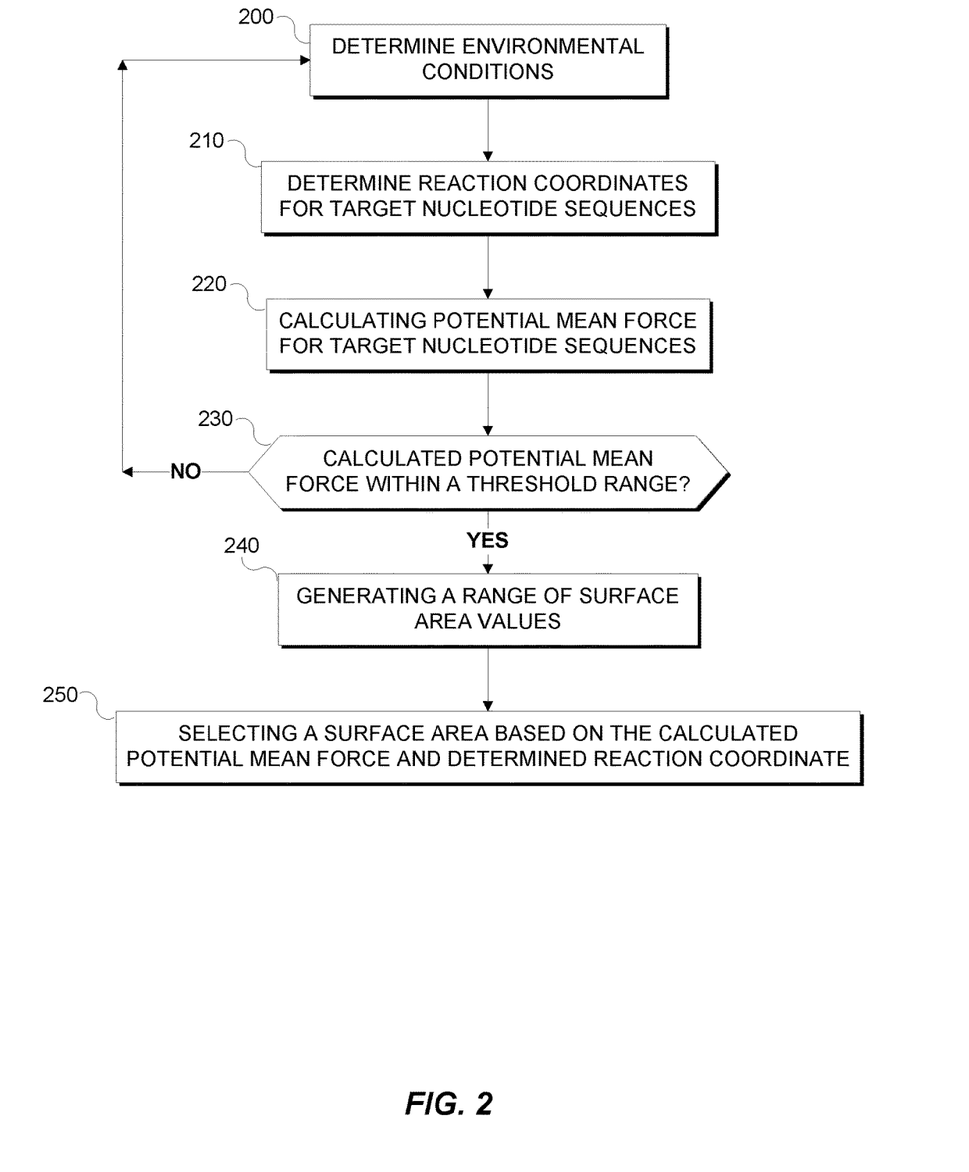
FIG. 2 is a flowchart depicting the method for designing a patterned nanometer length gold surface to improve hybridization.

FIG. 2 is a flowchart depicting the method for designing a patterned nanometer length gold surface to improve hybridization. In step 200, biosensor application 111 determines environmental conditions by receiving environmental data as described above. Step 210, biosensor application 111 determines the reaction coordinates for target nucleotide sequences by determining center-to-center distance between two nucleotide strands. The reaction coordinates may be a predetermined range, for example, ranging between 10 Å and 138 Å.

In step 220, biosensor application 111 calculates the potential of mean force (PMF) for target nucleotide sequences as described above. Biosensor application 111 calculates a range of PMF that is associated with nucleotide sequence length or reaction coordinates where the PMF of the nucleotide sequences is less than the repulsive layer potential values, in step 230. In step 240, a range of surface area values is generated based calculated threshold range, for example, if nucleotide sequences with a PMF less than the repulsive potential have a length of 40 Å to 80 Å, the range of surface area values is 4 nm to 8 nm as described above.

In step 250, an optimal surface area value is selected based on the maximum differential in nucleotide PMF and repulsive potential or a user selection of a length based on a generated graphical representation of PMF values (y-axis) versus reaction coordinate values (x-axis).

In various embodiments, the surface area value is verified via a manufactured biosensor, for example, biosensor 120. Biosensor 120 is manufactured based on the selected surface area value and hybridization data is received from the manufactured biosensor in order to verify the results of hybridization at selected surface area value of the nucleotide structures under test.

Figure 3:
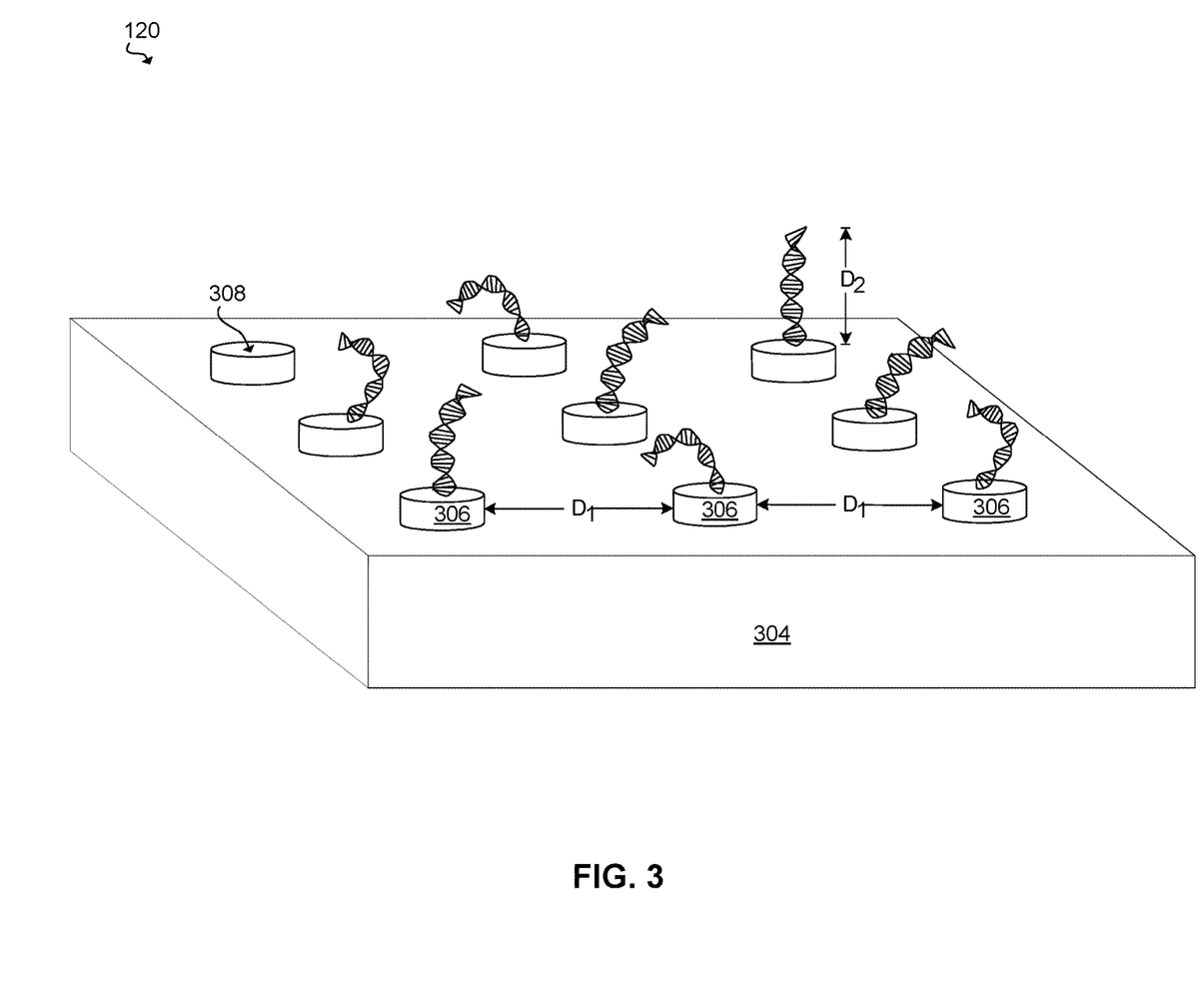
FIG. 3 depicts an exemplary biosensor, in accordance with an embodiment of the present invention.

FIG. 3 depicts an exemplary biosensor 120, in accordance with an embodiment of the present invention. Biosensor 120 may be manufactured based various surface area values and communicate hybridization population data to biosensor application 111 via server 110 through network 130. Biosensor application 111 may confirm optimal surface area values selection based on received data from biosensor 120. The structure of biosensor 120 is shown, according to an embodiment of the invention. The biosensor structure may be used to detect one or more target analyte and confirm selected surface area described above. For example, the target analyte detected by biosensor 120 may be a nucleotide sequence as described above. Remaining cylindrical portion (s) of the analyte affinity layer 306 may attract the nucleotide sequence and/or enable more complete nucleotide hybridization by holding corresponding nucleotide sequences within proximity to one another. An upper surface of the first dielectric layer 304 (e.g., composed of silicon oxide) may repel the nucleotide sequence. Due to a small area of the upper surface 308 of the remaining cylindrical portion of the analyte-affinity layer 306, only a fully formed pair of nucleotides may stay on the upper surface of the remaining cylindrical portion. The upper surface 308 may be have a diameter based on the optimal surface area For example, the upper surface 308 of the remaining cylindrical portion of the analyte-affinity layer 106 may have a diameter ranging from approximately 2 nm to approximately 20 nm, and ranges there between. For example, the upper surface of the remaining cylindrical portion of the analyte-affinity layer 306 may be approximately 6 nm. A length, or reaction coordinate, $D_2$ of a nucleotide sequence may be used to determine a diameter of the upper surface 308. The upper surface diameter may be based on the selected surface area value described above. For example, if a target analyte is a nucleotide sequence having 15 base pairs, the upper surface 308 may have a diameter ranging from approximately 3 nm to approximately 5 nm. In another example, if a target analyte is a nucleotide sequence having 50 base pairs, the upper surface 308 may have a diameter ranging from approximately 5 nm to approximately 15 nm.

Since the remaining cylindrical portions may be separated by the distance $D_1$, a target analyte may only adhere to a single cylindrical portion. In addition, the first dielectric layer may be composed of silicon oxide, which may repel particular analytes (e.g., a nucleotide sequence). By including isolated analyte-attracting points (e.g., separated gold portions) separated by an analyte repelling region (e.g., an upper surface of the first dielectric layer 304), analyte adhesion to the surface of the biosensor may be more precisely controlled and measured than previously possible with conventional devices.

Figure 4:
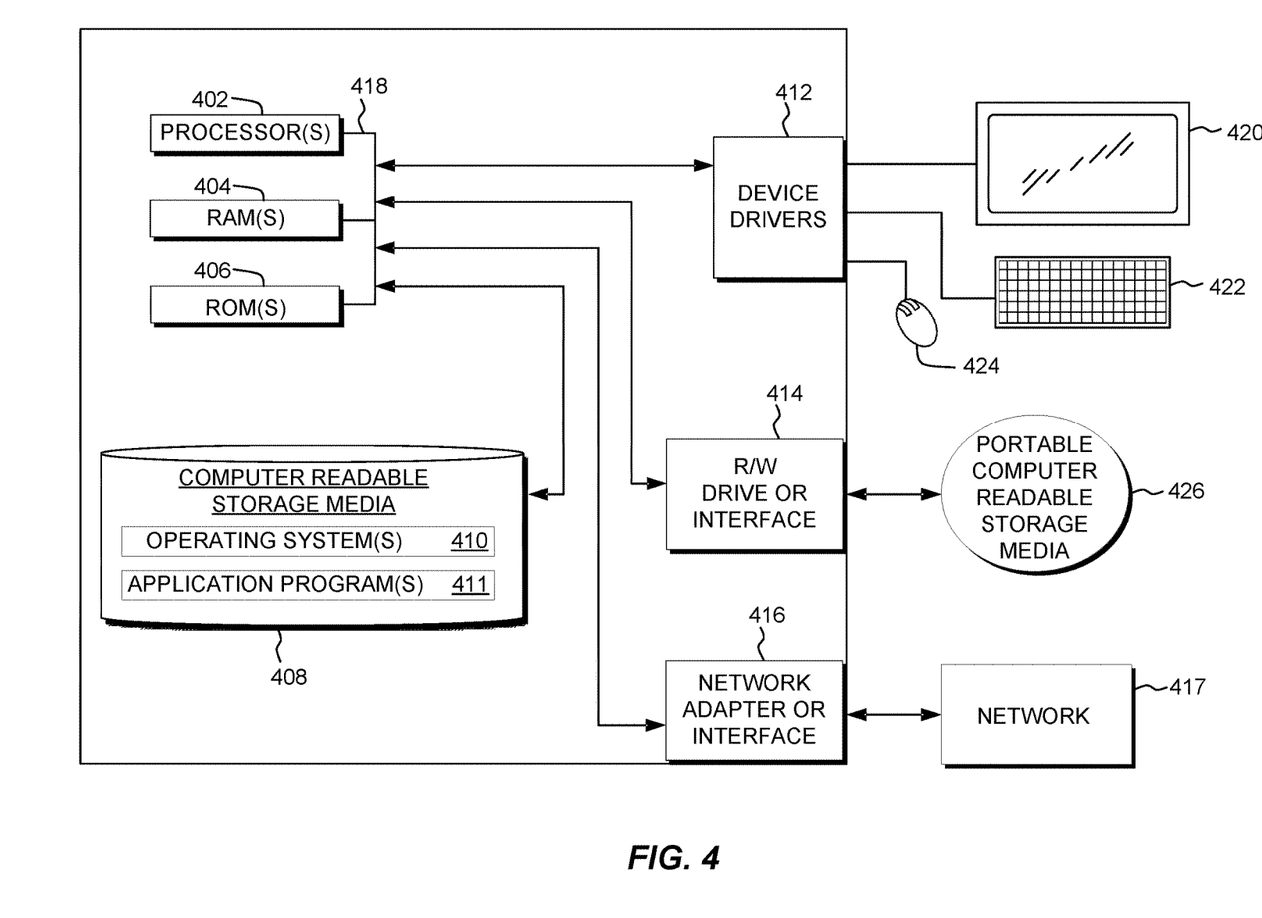
FIG. 4 depicts a block diagram of components of a computer executing the method, in accordance with an embodiment of the present invention.

Referring now to FIG. 4, FIG. 4 depicts a block diagram of components of server 110 of distributed data environment 100 of FIG. 1, in accordance with an embodiment of the present invention. It should be appreciated that FIG. 4 provides only an illustration of one implementation and does not imply any limitations with regard to the environments in which different embodiments may be implemented. Many modifications to the depicted environment may be made.

Server 110 may include one or more processors 402, one or more computer-readable RAMs 404, one or more computer-readable ROMs 406, one or more computer readable storage media 408, device drivers 412, read/write drive or interface 414, network adapter or interface 416, all interconnected over a communications fabric 418. Communications fabric 418 may be implemented with any architecture designed for passing data and/or control information between processors (such as microprocessors, communications and network processors, etc.), system memory, peripheral devices, and any other hardware components within a system.

One or more operating systems 410, and one or more application programs 411, for example, biosensor application 111, are stored on one or more of the computer readable storage media 408 for execution by one or more of the processors 402 via one or more of the respective RAMs 404 (which typically include cache memory). In the illustrated embodiment, each of the computer readable storage media 408 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Server 110 may also include an R/W drive or interface 414 to read from and write to one or more portable computer readable storage media 426. Application programs 411 on server 110 may be stored on one or more of the portable computer readable storage media 426, read via the respective R/W drive or interface 414 and loaded into the respective computer readable storage media 408.

Server 110 may also include a network adapter or interface 416, such as a TCP/IP adapter card or wireless communication adapter (such as a 4G wireless communication adapter using OFDMA technology) for connection to a network 417. Application programs 411 on server 110 may be downloaded to the computing device from an external computer or external storage device via a network (for example, the Internet, a local area network or other wide area network or wireless network) and network adapter or interface 416. From the network adapter or interface 416, the programs may be loaded onto computer readable storage media 408. The network may comprise copper wires, optical fibers, wireless transmission, routers, firewalls, switches, gateway computers and/or edge servers.

Server 110 may also include a display screen 420, a keyboard or keypad 422, and a computer mouse or touchpad 424. Device drivers 412 interface to display screen 420 for imaging, to keyboard or keypad 422, to computer mouse or touchpad 424, and/or to display screen 420 for pressure sensing of alphanumeric character entry and user selections. The device drivers 412, R/W drive or interface 414 and network adapter or interface 416 may comprise hardware and software (stored on computer readable storage media 408 and/or ROM 406).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

What is claimed is:

1. A method for manufacturing a biosensor structure for use in a biosensor device, the biosensor structure having an optimal hybridization surface area size identified based on a plurality of nucleotides structures under test, comprising:
   forming a first dielectric layer on a surface of the biosensor device;
   forming an analyte affinity layer on an upper surface of the first dielectric layer having a hybridization upper surface area size determined by:
   determining a first set of properties comprising reaction coordinate values, and potential of mean force (PMF) values, for the plurality of nucleotide structures based on a first set of testing conditions comprising a first surface area material, a first surface area pattern, and a first surface area size of a biosensing structure;
   determining a second set of properties comprising reaction coordinate values, and PMF values, for the plurality of nucleotide structures based on a second set of testing conditions comprising a second surface area material, a second surface area pattern, a second surface area size, or a combination thereof;
   identifying a target population of nucleotide structures among the plurality of nucleotide structures, the target population comprising nucleotide structures whose PMF values in the second set of properties are less than corresponding PMF values in the first set of properties;
   generating a graphical representation based on the identified target population of nucleotide structures, wherein the graphical representation compares PMF values and reaction coordinate values associated with the identified target population of nucleotide structures;
   determining an optimal hybridization surface area size based on the compared PMF values and reaction coordinate values associated with the identified target population of nucleotide structures;
   displaying the graphical representation and the calculated optimal hybridization surface area size to a user via a user device; and receiving from the user, via the user device, a user input selection of a surface area value, based on the displayed generated graphical representation the calculated optimal hybridization surface area size.

2. The method of claim 1, further comprising:
determining a third set of properties comprising reaction coordinate values, and PMF values, for at least the target population of nucleotide structures, based on a third set of testing conditions comprising a third surface area material, a third surface area pattern, a third surface area size, or a combination thereof; and
identifying which of the second and third sets of properties have the greatest difference compared to the first set of properties.

3. The method of claim 1, wherein the first set of testing conditions comprises:
the first surface area material comprising gold, silicon oxide, or both; and
the first surface area pattern comprises one or more of a sheet and a plurality of dots, wherein the first surface area size for the sheet is the area of the sheet, and the surface area size for the plurality of dots is the area of the top surfaces of the dots.

4. The method of claim 2 wherein the third surface area material is the same as the second surface area material, and the third surface area pattern is different from the second surface area pattern.

5. The method of claim 2, wherein the third surface area material is different from the second surface area material and the third surface area pattern is the same as the second surface area pattern.

6. The method of claim 2, wherein the third surface area material is the same as the second surface area material, the third surface area pattern is the same as the second surface area pattern, and the third surface area size is different from the second surface area size.

7. The method of claim 2, wherein the second and third sets of properties have the greatest difference compared to the first set of properties further comprises one or more of:
the second and third sets of properties having the largest area of PMF values below the PMF values of the first set of properties;
the second and third sets of properties with the largest negative slope;
the second and third sets of properties with the greatest delta value compared to the first set of properties; and
the second and third sets of properties with the lowest absolute PMF value.

8. The method of claim 7, wherein
the lowest absolute PMF value is within a range constrained by a first and second threshold, the first threshold being based on one or more of: a probe length value and a max probe energy value; and
the second threshold is based on one or more of: the determined reaction coordinate value and a repulsive surface PMF value.

9. A computer program product for manufacturing a biosensor structure for use in a biosensor device, the biosensor structure having an optimal hybridization surface area size identified based on a plurality of nucleotides structures under test, the computer program product comprising:
one or more non-transitory computer-readable storage media and program instructions stored on the one or more computer-readable storage media, the program instructions comprising:

instructions to form a first dielectric layer on a surface of the biosensor device;
instructions to form an analyte affinity layer on an upper surface of the first dielectric layer having a hybridization upper surface area size determined by:
instructions to determine a first set of properties comprising reaction coordinate values, and potential of mean force (PMF) values, for the plurality of nucleotide structures based on a first set of testing conditions comprising a first surface area material, a first surface area pattern, and a first surface area size of a biosensing structure;
instructions to determine a second set of properties comprising reaction coordinate values, and PMF values, for the plurality of nucleotide structures based on a second set of testing conditions comprising a second surface area material, a second surface area pattern, a second surface area size, or a combination thereof;
instructions to identify a target population of nucleotide structures among the plurality of nucleotide structures, the target population comprising nucleotide structures whose PMF values in the second set of properties are less than corresponding PMF values in the first set of properties;
instructions to generate a graphical representation based on the identified target population of nucleotide structures, wherein the graphical representation compares PMF values and reaction coordinate values associated with the identified target population of nucleotide structures;
instructions to determine an optimal hybridization surface area size based on the compared PMF values and reaction coordinate values associated with the identified target population of nucleotide structures;
instructions to display the graphical representation and the calculated optimal hybridization surface area size to a user via a user device; and
instructions to receive from the user, via the user device, a user input selection of a surface area value, based on the displayed generated graphical representation the calculated optimal hybridization surface area size.

10. The computer program product of claim 9, further comprising:
instructions to determine a third set of properties comprising reaction coordinate values, and PMF values, for at least the target population of nucleotide structures, based on a third set of testing conditions comprising a third surface area material, a third surface area pattern, a third surface area size, or a combination thereof; and
instructions to identify which of the second and third sets of properties have the greatest difference compared to the first set of properties.

11. The computer program product of claim 9, wherein the first set of testing conditions comprises:
the first surface area material comprising gold, silicon oxide, or both; and
the first surface area pattern comprises one or more of a sheet and a plurality of dots, wherein the first surface area size for the sheet is the area of the sheet, and the surface area size for the plurality of dots is the area of the top surfaces of the dots.

12. The computer program product of claim 10, wherein the third surface area material is the same as the second surface area material, and the third surface area pattern is different from the second surface area pattern.

13. The computer program product of claim 10, wherein the third surface area material is different from the second surface area material and the third surface area pattern is the same as the second surface area pattern.

14. The computer program product of claim 10, wherein the third surface area material is the same as the second surface area material, the third surface area pattern is the same as the second surface area pattern, and the third surface area size is different from the second surface area size.

15. The computer program product of claim 10, wherein the second and third sets of properties have the greatest difference compared to the first set of properties further comprises one or more of:
   the second and third sets of properties having the largest area of PMF values below the PMF values of the first set of properties;
   the second and third sets of properties with the largest negative slope;
   the second and third sets of properties with the greatest delta value compared to the first set of properties; and
   the second and third sets of properties with the lowest absolute PMF value.

16. The computer program product of claim 15, wherein the lowest absolute PMF value is within a range constrained by a first and second threshold, the first threshold being based on one or more of: a probe length value and a max probe energy value; and
   the second threshold is based on one or more of: the determined reaction coordinate value and a repulsive surface PMF value.

17. A computer system for manufacturing a biosensor structure for use in a biosensor device, the biosensor structure having an optimal hybridization surface area size identified based on a plurality of nucleotides structures under test, the computer system comprising:
   one or more computer processors;
   one or more computer-readable storage media;
   program instructions stored on the computer-readable storage media for execution by at least one of the one or more processors, the program instructions comprising:
   instructions to form a first dielectric layer on a surface of the biosensor device;
   instructions to form an analyte affinity layer on an upper surface of the first dielectric layer having a hybridization upper surface area size determined by:
   instructions to determine a first set of properties comprising reaction coordinate values, and potential of mean force (PMF) values, for the plurality of nucleotide structures based on a first set of testing conditions comprising a first surface area material, a first surface area pattern, and a first surface area size of a biosensing structure;
   instructions to determine a second set of properties comprising reaction coordinate values, and PMF values, for the plurality of nucleotide structures based on a second set of testing conditions comprising a second surface area material, a second surface area pattern, a second surface area size, or a combination thereof;
   instructions to identify a target population of nucleotide structures among the plurality of nucleotide structures, the target population comprising nucleotide structures whose PMF values in the second set of properties are less than corresponding PMF values in the first set of properties;
   instructions to generate a graphical representation based on the identified target population of nucleotide structures, wherein the graphical representation compares PMF values and reaction coordinate values associated with the identified target population of nucleotide structures;
   instructions to determine an optimal hybridization surface area size based on the compared PMF values and reaction coordinate values associated with the identified target population of nucleotide structures;
   instructions to display the graphical representation and the calculated optimal hybridization surface area size to a user via a user device; and
   instructions to receive from the user, via the user device, a user input selection of a surface area value, based on the displayed generated graphical representation the calculated optimal hybridization surface area size.

18. The computer system of claim 17, further comprising:
   instructions to determine a third set of properties comprising reaction coordinate values, and PMF values, for at least the target population of nucleotide structures, based on a third set of testing conditions comprising a third surface area material, a third surface area pattern, a third surface area size, or a combination thereof; and
   instructions to identify which of the second and third sets of properties have the greatest difference compared to the first set of properties.

* * * * *